US010624989B2

(12) United States Patent
Serrero et al.

(10) Patent No.: US 10,624,989 B2
(45) Date of Patent: Apr. 21, 2020

(54) IMPLANT COMPRISING OXIDIZED CELLULOSE AND METHOD FOR PREPARING SUCH AN IMPLANT

(71) Applicant: Sofradim Production, Trévoux (FR)

(72) Inventors: Aurelie Serrero, Lyons (FR); Robert Vestberg, Lyons (FR); Suzelei Montanari, Trevoux (FR)

(73) Assignee: Sofradim Production, Trévoux (FR)

( * ) Notice: Subject to any disclaimer, the term of this patent is extended or adjusted under 35 U.S.C. 154(b) by 0 days.

(21) Appl. No.: 16/424,543

(22) Filed: May 29, 2019

(65) Prior Publication Data

US 2019/0275202 A1 Sep. 12, 2019

Related U.S. Application Data

(63) Continuation of application No. 15/314,557, filed as application No. PCT/EP2015/062017 on May 29, 2015, now Pat. No. 10,328,178.

(30) Foreign Application Priority Data

May 30, 2014 (EP) ..................................... 14305820

(51) Int. Cl.
*A61L 27/20* (2006.01)
*A61L 27/34* (2006.01)
(Continued)

(52) U.S. Cl.
CPC ........... *A61L 27/20* (2013.01); *A61L 24/0042* (2013.01); *A61L 24/043* (2013.01); *A61L 27/34* (2013.01);
(Continued)

(58) Field of Classification Search
None
See application file for complete search history.

(56) References Cited

U.S. PATENT DOCUMENTS

| 3,364,200 A | 1/1968 | Ashton et al. |
| 4,378,431 A | 3/1983 | Brown, Jr. |

(Continued)

FOREIGN PATENT DOCUMENTS

| EP | 0396344 A2 | 11/1990 |
| EP | 1389450 A1 | 2/2004 |

(Continued)

OTHER PUBLICATIONS

Coln, D. ; Horton, J. ; Ogden, M.E. ; Buja, L., "Evaluation of hemostatic agents in experimental splenic lacerations", American Journal of Surgery, Paul Hoeber, New York, NY, US, US, (Feb. 1, 1983), vol. 145, No. 2, ISSN 0002-9610, pp. 256-259, XP026418142.

(Continued)

*Primary Examiner* — Carlos A Azpuru
*Assistant Examiner* — Casey S Hagopian

(57) ABSTRACT

The present invention relates to an implant (10) comprising: a substrate (1) the surface of which comprising oxidized cellulose, said oxidized cellulose having a degree of oxidation ranging from 0.5 to 1, and a multilayer coating covering said substrate, said multilayer coating comprising at least a first layer (2) adjacent said substrate, said first layer being formed of chitosan, and a second layer (3) adjacent said first layer, said second layer being formed of oxidized cellulose having a degree of oxidation ranging from 0.5 to 1. The invention further relates to a method for preparing such an implant.

18 Claims, 2 Drawing Sheets

Figure 1A:
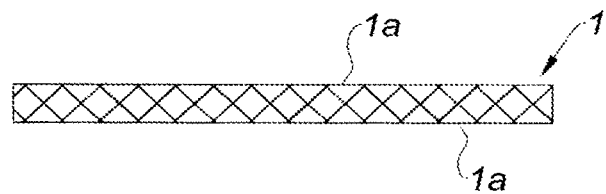

(51) Int. Cl.
  *A61L 27/58* (2006.01)
  *A61L 31/04* (2006.01)
  *A61L 31/10* (2006.01)
  *A61L 31/14* (2006.01)
  *A61L 24/00* (2006.01)
  *A61L 24/04* (2006.01)
  *A61L 27/56* (2006.01)

(52) U.S. Cl.
  CPC ............... *A61L 27/56* (2013.01); *A61L 27/58* (2013.01); *A61L 31/042* (2013.01); *A61L 31/10* (2013.01); *A61L 31/146* (2013.01); *A61L 31/148* (2013.01); *A61L 2400/04* (2013.01); *A61L 2420/08* (2013.01)

(56) References Cited

U.S. PATENT DOCUMENTS

| | | |
|---|---|---|
| 4,553,272 A | 11/1985 | Mears |
| 4,588,400 A | 5/1986 | Ring et al. |
| 4,655,758 A | 4/1987 | Ring et al. |
| 4,788,146 A | 11/1988 | Ring et al. |
| 4,912,049 A | 3/1990 | Farah |
| 5,326,356 A | 7/1994 | Della et al. |
| 5,955,326 A | 9/1999 | Bungay, III et al. |
| 6,071,727 A | 6/2000 | Bungay et al. |
| 6,391,059 B1 | 5/2002 | Lemperle et al. |
| 6,443,964 B1 | 9/2002 | Ory et al. |
| 6,451,032 B1 | 9/2002 | Ory et al. |
| 6,777,227 B2 | 8/2004 | Ricci et al. |
| 6,946,003 B1 | 9/2005 | Wolowacz et al. |
| 7,390,492 B1 | 6/2008 | Mansfield et al. |
| 7,709,631 B2 | 5/2010 | Harris et al. |
| 8,962,006 B2 | 2/2015 | Bayon et al. |
| 2003/0064089 A1* | 4/2003 | Kumar ............... A61L 27/20 424/423 |
| 2004/0182261 A1 | 9/2004 | Fernfors et al. |
| 2005/0228329 A1 | 10/2005 | Boehringer et al. |
| 2006/0147612 A1 | 7/2006 | Da Rocha |
| 2007/0032805 A1 | 2/2007 | Therin et al. |
| 2007/0128243 A1 | 6/2007 | Serafica et al. |
| 2007/0213522 A1 | 9/2007 | Harris et al. |
| 2009/0068250 A1* | 3/2009 | Gravagna ............... A61L 27/24 424/426 |
| 2009/0069904 A1 | 3/2009 | Picha |
| 2009/0216338 A1 | 8/2009 | Gingras et al. |
| 2011/0087273 A1 | 4/2011 | Stopek et al. |

FOREIGN PATENT DOCUMENTS

| | | | | |
|---|---|---|---|---|
| EP | 1952828 A2 * | 8/2008 | ........... | A61K 31/717 |
| EP | 1952828 A2 | 8/2008 | | |
| EP | 1953174 A1 | 8/2008 | | |
| WO | 9310731 A1 | 6/1993 | | |
| WO | 9905990 A1 | 2/1999 | | |
| WO | 0180774 A1 | 11/2001 | | |
| WO | 2004045458 A1 | 6/2004 | | |
| WO | 2006018552 A1 | 2/2006 | | |
| WO | 2006042287 A2 | 4/2006 | | |
| WO | 2007106251 A1 | 9/2007 | | |
| WO | 2008079034 A2 | 7/2008 | | |
| WO | 2009031035 A2 | 3/2009 | | |
| WO | 2009071998 A2 | 6/2009 | | |
| WO | 2014048982 A1 | 4/2014 | | |

OTHER PUBLICATIONS

Helenius et al., In vivo biocompatibility of bacterial celullose, Wiley InterScience, Nov. 2005, pp. 431-438.

International Search Report for PCT/EP2015/062017 dated Jun. 25, 2015 (3 pages).

João P. De Mesquita, Claudio L. Donnici, Fabiano V. Pereira, "Biobased Nanocomposites from Layer-by-Layer Assembly of Cellulose Nanowhiskers with Chitosan", Biomacromolecules, American Chemical Society, (Feb. 8, 2010), vol. 11, No. 2, doi:10.1021/bm9011985, ISSN 15257797, pp. 473-480, XP055133947.

Lamarque, G. et al, "New Route of Deacetylation of alpha- and beta-Chitins by Means of Freeze-Pump Out-Thaw Cycles" Biomacromolecules, May-Jun. 2005, pp. 1380-1388, 6.

Lamarque, G. et al., "Comparative Study of the Second and Third Heterogeneous Deacetylations of alpha- and beta-Chitins in a Multistep Process" Biomacromolecules, Sep.-Oct. 5, 2004, pp. 1899-1907, 5.

Lamarque, G. et al., Comparative Study of the First Heterogeneous Deacetylation of alpha- and beta-Chitins in a Multistep Process Biomacromolecules May-Jun. 2004, 992-1001, 5.

Pommet et al., "Surface Modification of Natural Fibers Using Bacteria: Depositing Bacterial Cellulose onto Natural Fibers to Create Hierarchical Reinforced Nanocomposites," Biomacromolecules, May 2008, pp. 1643-1651, vol. 9, No. 3.

Richardson, et al., "Characterisation of the substituent distribution in starch and cellulose derivatives," Analytica Chimica Acta, Aug. 2003, pp. 27-65, vol 497.

Tolaimate, A., et al. "Contribution to the preparation of chitins and chitosans with controlled physico-chemical properties." Polymer, Dec. 2003, pp. 7939-7952, 44 (26).

Uraki et al., "Honeycomb-like Architecture Produced by Living Bacteria", vol. 69, No. 1, Mar. 30, 2007, Abstract only.

Wayne Halfpenny, Julian S. Fraser, David M. Adlam, "Comparison of 2 hemostatic agents for the prevention of postextraction hemorrhage in patients on anticoagulants", Oral Surgery, Oral Medicine, Oral Pathology, Oral Radiology & Endodontics, (Sep. 1, 2001), vol. 92, No. 3, doi:10.1067/moe.2001.115463, ISSN 10792104, pp. 257-259, XP055134056.

* cited by examiner

IMPLANT COMPRISING OXIDIZED CELLULOSE AND METHOD FOR PREPARING SUCH AN IMPLANT

CROSS-REFERENCE TO RELATED APPLICATIONS

This application is a continuation of U.S. patent application Ser. No. 15/314,557 filed Nov. 29, 2016, which is a National Stage Application of PCT/EP2015/062017 filed May 29, 2015, which claims benefit of and priority to European Patent Application Serial No. 14305820.4 filed May 30, 2014, and the disclosures of each of the above-identified applications are hereby incorporated by reference in their entirety.

The present invention relates to implants comprising a substrate the surface of which comprises oxidized cellulose and a coating applied on said substrate.

These implants may be used, for example, as haemostatic patches, adhesion prevention barriers, or as wall reinforcements in the repair, reinforcement or replacement of soft tissues.

Oxidized cellulose is of high interest in the field of medical implants. Oxidized cellulose is a highly biocompatible material, showing properties such as high moisture, handling ability which can help the repair, reinforcement or replacement of soft tissues.

Oxidized cellulose has bactericidal effects towards a wide spectrum of aerobic and anaerobic pathogens and therefore shows a therapeutic potential for use in medical implants in general.

In addition, thanks to its good haemostatic effects, biosolubility and biodegradability, antioxidant and wound-healing properties, oxidized cellulose represents a suitable means for the therapy of bleeding conditions in various fields of medicine. As such, oxidized cellulose may advantageously constitute the absorbent substrate of a haemostatic patch.

Anyway, it has been observed that non bioresorbable oxidized cellulose could trigger an undesirable immune response from the body once implanted. On the contrary, for some applications, bioresorbable oxidized cellulose degrades too rapidly in physiological conditions: the mechanical properties of the implant disappear before the implant had time to perform its intended function, thereby jeopardizing the success of the surgical operation.

For the purpose of the present application, the term "bioresorbable" is intended to mean the characteristic according to which a material is degraded by the biological tissues and the surrounding fluids, in vivo after a given period of time, that may vary, for example, from a few hours to several months, depending on the chemical nature of the material.

Haemostatic patches are implantable medical devices for stopping the flow of biological fluids such as blood during surgery. Permanent implants are not always necessary for use as haemostatic patches. For example, bioresorbable or partly-bioresorbable haemostatic patches may be made to at least partly disappear in vivo after implantation, after a few weeks for example, when their function of stopping the effusion of biological fluids is no longer necessary.

Permanent implants are neither always essential for the repair, reinforcement or replacement of soft tissues. For example, in the case of treatment of certain defects such as for the treatment of hernias or reconstruction of a visceral wall, one may seek to limit the amount of foreign bodies which remain permanently in a human body and promote tissue reconstruction.

Thus, it would be desirable to provide an implant provoking no immune response from the body once implanted, this implant having nevertheless a substrate comprising oxidized cellulose, where this oxidized cellulose would show a degradation time sufficiently delayed so that the implant would be capable of performing its intended function.

The Applicant has found that by applying a particular coating on a substrate the surface of which comprises a specific oxidized cellulose, it was possible to obtain an implant comprising oxidized cellulose capable of having a degradation time in vivo sufficient for obtaining the intended results expected from the presence of oxidized cellulose while avoiding problematic immune response from the body.

A first aspect of the invention is an implant comprising:
 a substrate the surface of which comprising at least oxidized cellulose, said oxidized cellulose having a degree of oxidation ranging from 0.5 to 1, and
 a multilayer coating covering said substrate, said multilayer coating comprising at least a first layer adjacent the surface of said substrate, said first layer being formed of chitosan, and a second layer adjacent said first layer, said second layer being formed of oxidized cellulose having a degree of oxidation ranging from 0.5 to 1.

The implant of the invention is at least partly bioresorbable. In the implant of the invention, the oxidized cellulose present at least at the surface of the substrate is bioresorbable and shows a degradation time in physiological conditions compatible with the function the implant is intended to perform. The implant of the invention therefore allows providing at least partly bioresorbable implants comprising oxidized cellulose having both a significant degradation time in vivo and furthermore showing the properties of oxidized cellulose in general, such as biocompatibility, antioxidant and haemostatic properties, bactericidal properties, etc. . . .

Another aspect of the invention is a method for preparing an implant as described herein, comprising the following steps:
 i) providing a substrate the surface of which comprising at least oxidized cellulose, said oxidized cellulose having a degree of oxidation ranging from 0.5 to 1,
 ii) providing a solution of chitosan,
 iii) providing a solution of oxidized cellulose having a degree of oxidation ranging from 0.5 to 1,
 iv) covering said substrate with a part of the solution of chitosan of ii) for forming a first layer adjacent the surface of said substrate,
 v) covering the one layer coated substrate obtained in step iv) with a part of the solution of oxidized cellulose of iii) for forming a second layer adjacent said first layer,
 vi) optionally repeating steps iv) and v) as many times as desired.

Figure 1B:
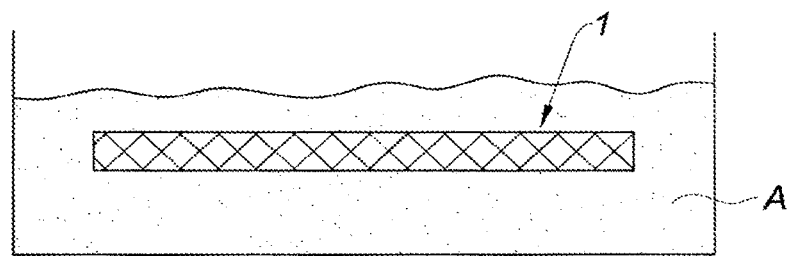
Figure 1C:
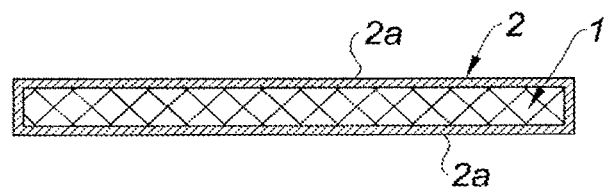
Figure 1D:
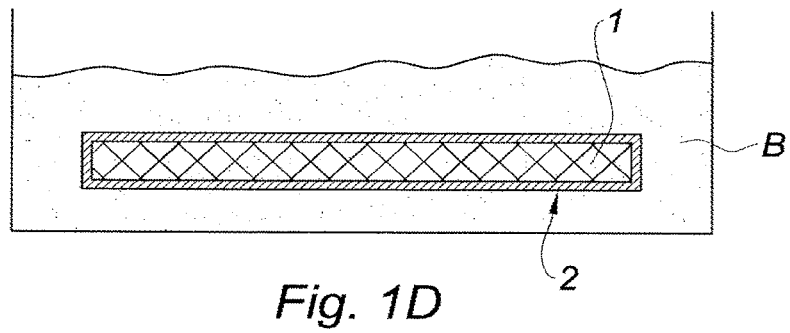
Figure 1E:
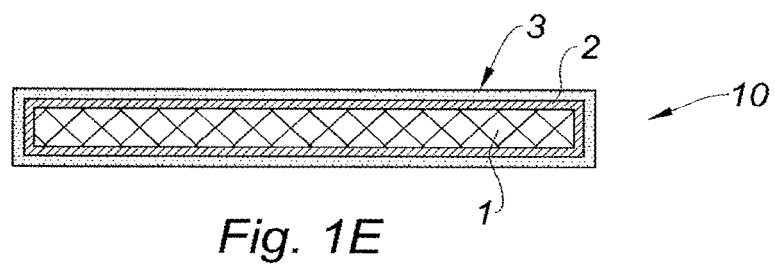
Figure 2A:
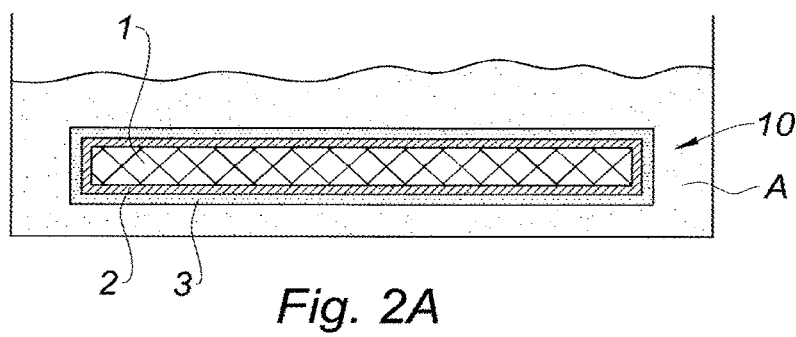
Figure 2B:
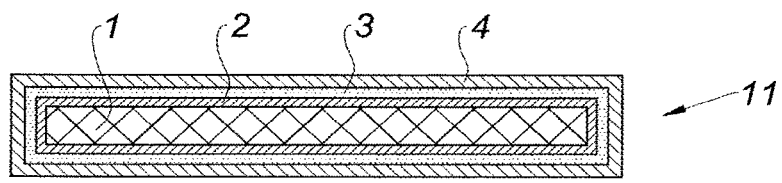

The advantages of the invention will be better understood in view of the detailed description that follows and with the help of the accompanying drawings in which:

FIGS. 1A-1E are cross section views showing the preparation of an embodiment of an implant according to the invention, with a first layer formed of chitosan and a second layer formed of oxidized cellulose, FIGS. 2A-2B are cross section views showing the preparation of another embodiment of an implant of the invention, provided with a third layer, formed of chitosan.

The implant of the present invention comprises a substrate the surface of which comprises at least oxidized cellulose, said oxidized cellulose having a degree of oxidation ranging from 0.5 to 1.

Oxidized cellulose is a known material. It can for example be selected from oxidized cellulose, where the $C_6$ primary alcohol is partially or fully oxidized to carboxylic acid, for example to give polyglucuronic acid, oxidized cellulose in the form of polyaldehydes by periodic acid, and mixtures thereof. The cellulose used for oxidation can be obtained from type I cellulose or can be regenerated.

Several types of regenerated cellulose have been developed industrially. We may mention for example the "viscose" process, which is based on the solubility of cellulose xanthate in a dilute solution of sodium hydroxide. We may also mention the so-called "cupro-ammonium process" employed for example by the company Bemberg in Italy or the company Asahi Chemical Industries in Japan, which consists of dissolving cellulose in an ammoniacal solution of copper. Another method of preparing regenerated cellulose suitable for the present invention is the method of organic-phase dissolution of cellulose by N-methylmorpholine oxide (N.M.M.O.), called the "Lyocell® process", employed for example by the company Lenzing in Austria.

The oxidized cellulose of the substrate of the implant of the invention shows a degree of oxidation ranging from 0.5 to 1. An oxidized cellulose with such a degree of oxidation is bioresorbable. The preparation of such an oxidized cellulose is described in WO2006/018552.

Oxidized cellulose of degree of oxidation ranging from 0.5 to 1 may also be commercially available from company Ethicon under the tradename of "Surgicel®" or "Interceed®", or from company Covidien under the tradename of "Veriset®".

In embodiments, the oxidized cellulose present at least at the surface of the substrate of the implant of the invention shows a degree of oxidation of about 0.6. Such an oxidized cellulose is amorphic. In embodiments, for example, when it is desired to maximize the haemostatic efficiency of the oxidized cellulose, the oxidized cellulose shows a degree of oxidation ranging from 0.6 to 1.

Oxidized cellulose is a compound which is naturally negatively charged. The surface of the substrate of the implant of the invention is therefore negatively charged. In this view, the substrate of the implant of the invention may optionally further comprise other biocompatible bioresorbable or non bioresorbable materials in addition to oxidized cellulose of degree of oxidation ranging from 0.5 to 1, as long as its surface remains negatively charged. In particular, the substrate of the implant of the invention may further comprise a neutral material or a negatively charged material.

Suitable neutral non bioresorbable materials that may be included in the substrate of the implant of the invention may be selected from polypropylene, polyethylene terephthalate and combinations thereof. Suitable neutral bioresorbable materials that may be included in the substrate of the implant of the invention may be selected from polylactic acid, polyglycolic acid and combinations thereof. Suitable bioresorbable negatively charged materials that may be included in the substrate of the implant of the invention may be selected from polysaccharides such as alginate, hyaluronan and combinations thereof.

In embodiments, the implant of the invention is bioresorbable. For example, the substrate consists in bioresorbable materials only. Apart from the oxidized cellulose of degree of oxidation ranging from 0.5 to 1, these bioresorbable materials may be selected from polylactic acid, polyglycolic acid, polysaccharides such as alginate, hyaluronan, and combinations thereof. In embodiments, the substrate of the implant of the invention consists in said oxidized cellulose having a degree of oxidation ranging from 0.5 to 1. No other material is present in the substrate or at the surface of the substrate. In such embodiments, the implant of the invention is bioresorbable. The implant of the invention therefore shows a degradation time in vivo greater than the degradation time that would be that of the substrate taken on its own. The implant of the invention therefore allows providing fully bioresorbable implants comprising oxidized cellulose having both a significant degradation time in vivo and furthermore showing the properties of oxidized cellulose in general, such as biocompatibility, antioxidant and haemostatic properties, bactericidal properties, etc. . . .

The substrate of the implant of the present invention may show any form, shape or structure suitable for implantation inside a human or animal body, in adequation with the function the implant is intended to perform.

For example, the substrate may be under the form of porous or solid body. In a view of being used for forming either a haemostatic patch or a reinforcement wall, the substrate may preferably be under the form of a porous layer. In embodiments, the substrate is under the form of a porous layer.

In the present application, "porous layer" means a layer having pores, or voids, cells, holes, orifices, distributed regularly or irregularly, not only on the surface but also within the thickness of said layer, and more or less interconnected. Said porous layer is particularly effective for absorbing biological fluids such as blood and may be useful for forming a haemostatic patch. Such a porous layer is also effective for promoting cell colonization and may be useful for forming a reinforcement wall in hernia repair.

Such a porous layer may for example be under the form of a foam or a sponge, for example obtained by freeze-drying of a solution of oxidized cellulose, or under the form of an openwork textile.

According to the present application, "textile" means any arrangement or assemblage of biocompatible threads, fibres, filaments and/or multifilaments, for example obtained by knitting, weaving, braiding, or alternatively non-woven. The arrangement of threads of the textile according to the invention defines at least two opposite faces, a first face and a second face.

In the present application, "openwork textile" means any textile whose arrangement of threads of which it is constituted determines openings, cells or voids in the thickness of the textile and on the faces of the textile, and these openings, cells or voids can constitute channels with openings on either side of the textile. This openwork textile gives good absorption of biological fluids. Such an openwork textile also favors cell colonization.

In embodiments, the substrate is under the form of an openwork textile. The openwork textile may comprise yarns of oxidized cellulose having a degree of oxidation ranging from 0.5 to 1 and optionally additional yarns of biocompatible bioresorbable or non bioresorbable materials. In embodiments, the substrate consists in an openwork textile of oxidized cellulose having a degree of oxidation ranging from 0.5 to 1.

The openwork textile may be in the form of a two-dimensional or three-dimensional knitted fabric.

"Two-dimensional knitted fabric" means, in the sense of the present application, a knitted fabric having two opposite faces joined together by stitches but lacking cross-members giving it a certain thickness: a knitted fabric of this kind can be obtained for example by knitting threads on a warp knitting machine or Raschel machine using two guide bars. Examples of knitting of two-dimensional knitted fabrics suitable for the present invention are given in document WO2009/071998.

"Three-dimensional knitted fabric" means, according to the present application, a knitted fabric having two opposite faces joined together by a cross-member giving the knitted fabric a significant thickness, said cross-member itself being formed of additional connecting threads supplementary to the threads forming the two faces of the knitted fabric. This knitted fabric can be obtained for example on a warp knitting machine or double-bed Raschel machine using several guide bars. Examples of knitting of three-dimensional knitted fabrics suitable for the present invention are given in documents WO99/05990, WO2009/031035, WO2009/071998.

This kind of three-dimensional knitted fabric, with the presence of a spacer giving it a significant thickness, provides excellent absorption of biological fluids such as blood and is particularly suitable for manufacture of a haemostatic patch. Such a three-dimensional knitted fabric may alternatively be suitable for the manufacture of a reinforcement wall, as its porosity and significant thickness provides for an adequate medium and space for cell colonization.

A knitted fabric, in particular three-dimensional, based on oxidized cellulose, can be obtained by knitting firstly threads of unoxidized regenerated cellulose, then submitting the knitted fabric thus obtained to oxidation.

In fact, when spun through a perforated plate, viscose sets in an acid medium and forms long continuous filaments of regenerated cellulose, which are dried and combined in multifilament threads. A regenerated cellulose thread is obtained that has good mechanical strength.

Generally this regenerated cellulose thread is not bioresorbable. However, it has good mechanical strength allowing it to be used for manufacturing a knitted fabric. As an example, we may mention, as regenerated cellulose thread suitable for manufacturing a knitted fabric suitable for the porous layer of the patch of the invention, the 90 decitex multifilament thread marketed under the name "CUPRO® Cusio" by the Italian company Bemberg.

The knitted fabric obtained is then oxidized in order to form a porous layer based on oxidized cellulose suitable for forming the substrate of the implant according to the present invention. Such a knitted fabric may show a high porosity allowing tissue integration and is therefore particularly useful for the repair, reinforcement or replacement of soft tissues. Such a knitted fabric also shows good tensile strength allowing it to be fixed to tissues by any known techniques, such as suturing, stitching, stapling, tacking, and combinations thereof. In addition, as a textile, such a knitted fabric is easy to handle and may further be formed in a specific desired shape.

The implant of the invention further comprises a multilayer coating covering the substrate. The multilayer coating comprises at least a first layer adjacent the surface of said substrate, this first layer being formed of chitosan, and a second layer adjacent the first layer, this second layer being formed of oxidized cellulose having a degree of oxidation ranging from 0.5 to 1.

Chitosan is a biocompatible biopolymer obtained by deacetylation of chitin. Chitin is extracted from exoskeletons of arthropods such as the lobster, crab, prawn, the endoskeleton of cephalopods such as the squid, or from fungi. Extraction of chitin involves steps of hydrolysis of the proteins and lipids, depigmentation and demineralization. Hydrolysis of the proteins and lipids is usually carried out in the presence of sodium hydroxide, and demineralization requires the use of hydrochloric acid.

Once the chitin has been extracted, chitosan is obtained by a deacetylation step, which consists of hydrolysis of the acetamide groups. This reaction is generally carried out at high temperature in an alkaline solution, for example a 48% solution of sodium hydroxide (NaOH) in water, at 90° C. Chitosan is a compound that is soluble in aqueous solution and can have a degree of acetylation (DA) of up to 70%.

The following publications describe processes for deacetylation of chitin to obtain chitosan: "Lamarque, G., C. Viton, and A. Domard, *New Route of Deacetylation of α- and β-Chitins by means of Freeze-Pump Out-Thaw Cycles*. Biomacromolecules, 2005. 6(3): p. 1380-1388.", "Lamarque, G., C. Viton, and A. Domard, *Comparative Study of the First Heterogeneous Deacetylation of α- and β-Chitins in a Multistep Process*. Biomacromolecules, 2004. 5(3): p. 992-1001.", "Lamarque, G., C. Viton, and A. Domard, *Comparative Study of the Second and Third Heterogeneous Deacetylations of α- and β-Chitins in a Multistep Process*. Biomacromolecules, 2004. 5(5): p. 1899-1907.", "Tolaimate, A., et al., *Contribution to the preparation of chitins and chitosans with controlled physicochemical properties*. Polymer, 2003. 44(26): p. 7939-7952."

Chitosan is a bioresorbable compound. The degree of acetylation of chitosan can have an influence on the kinetics of degradation of chitosan. Thus, depending on the kinetics of biodegradation desired for the implant of the invention, the chitosan will have to have a degree of acetylation ranging from 0 to 70%.

In embodiments, the degree of acetylation of the chitosan is 30%.

The oxidized cellulose used for forming the second layer of the multilayer coating of the substrate of the implant of the invention may be defined in the same way as the oxidized cellulose defined above for the substrate of the implant. In particular, the oxidized cellulose used for forming the second layer of the multilayer coating of the substrate of the implant of the invention is a negatively charged compound. This oxidized cellulose shows a degree of oxidation ranging from 0.5 to 1 and is bioresorbable. In embodiments, this oxidized cellulose shows a degree of oxidation of 0.6. Such an oxidized cellulose is amorphic. In embodiments, the oxidized cellulose shows a degree of oxidation ranging from 0.6 to 1.

In embodiments, the multilayer coating further comprises a third layer adjacent the second layer, the third layer being formed of chitosan. The chitosan used for forming the third layer of the multilayer coating of the substrate of the implant of the invention may show the same degree of acetylation as the chitosan used for the first layer or on the contrary another degree of acetylation. The choice of the degree of acetylation of the chitosan for the first layer and of the chitosan of the third layer may depend on the desired degradation profile for the implant once implanted. An implant with a three-layer coating, namely a first layer of chitosan, a second layer of oxidized cellulose and a third layer of chitosan shows a prolonged degradation time in vivo with respect to an implant with no coating or that would be coated with one layer of chitosan only for example. It is therefore possible to provide an implant comprising oxidized cellulose and showing the properties of oxidized cellulose having in addition a delayed degradation time in vivo and therefore capable of performing its function of either a haemostatic patch or a wall reinforcement during a significant time. In further embodiments, the multilayer coating further comprises a fourth layer adjacent the third layer, said fourth layer being formed of oxidized cellulose having a degree of oxidation ranging from 0.5 to 1. In embodiments, the multilayer coating further comprises a fifth layer adjacent the fourth layer, said fifth layer being formed of chitosan. Such embodiments of the implant of the invention allow ensuring a long time performance of the oxidized cellulose present at least at the surface of the substrate.

The method for preparing the implant of the invention comprises the following steps:
  i) providing a substrate the surface of which comprising at least oxidized cellulose, said oxidized cellulose having a degree of oxidation ranging from 0.5 to 1,
  ii) providing a solution of chitosan,
  iii) providing a solution of oxidized cellulose having a degree of oxidation ranging from 0.5 to 1,
  iv) covering said substrate with a part of the solution of chitosan of ii) for forming a first layer adjacent the surface of said substrate,
  v) covering the one layer coated substrate obtained in step iv) with a part of the solution of oxidized cellulose of iii) for forming a second layer adjacent said first layer,
  vi) optionally repeating steps iv) and v) as many times as desired.

The multilayer coating of the implant of the invention is manufactured by applying the first, second and optionally third, fourth and fifth layers on the substrate by electrostatic layer-by-layer self assembly ("ELBL"). ELBL is a technique in which layers are assembled by alternating the adsorption of oppositely-charged polyelectrolytes. The process is based on the reversal of the surface charge of the coating after the deposition of each layer.

As seen above, the surface of the substrate comprising oxidized cellulose is negatively charged. Chitosan is a polycationic material and therefore a positively charged compound. A first layer of chitosan is applied on the surface of the substrate comprising oxidized cellulose. The coating of the substrate therefore becomes positively charged. A second layer, of negatively charged oxidized cellulose, is then applied on the first layer of chitosan. The coating becomes negatively charged. A third layer, of positively charged chitosan is then applied on the second layer. The coating becomes positively charged again.

The physical basis of association is electrostatics. The application of alternately charged layers may be repeated as many times as needed.

For the manufacture of the multilayer coating as describe above, solutions of chitosan and solutions of oxidized cellulose are prepared, and the substrate may be successively covered by parts of these solutions.

The chitosan solution is generally prepared starting from a solution of chitosan in acidic water. The concentration of chitosan in said solution may range for example from 0.01% to 1%, by weight, relative to the total weight of the solution. The concentration of chitosan in the solution may depend on the molecular weight of the chitosan used. For example, for chitosan of high molecular weight, the concentration may be chosen in the low part of the range given above, so that the molecules of chitosan have enough space not to become entangled, and thereby efficiently leading to the formation of a complex between the various layers of the coating of the implant of the invention. Sodium chloride (NaCl) may be added to the solution. The pH of the solution usually ranges from 1.5 to 7.

The oxidized cellulose solution is generally prepared by dissolving oxidized cellulose in water. Caustic soda may be added to the solution. The concentration of oxidized cellulose in said solution may range for example from 0.01% to 1%, by weight, relative to the total weight of the solution. Acid, such as chlorohydric acid, may be added to the solution in order to adjust the pH from 3 to 7. The oxidized cellulose concentration is determined in function of the intended degradation profile of the layer which will be formed. Sodium chloride (NaCl) may be added to the solution.

In embodiments, step iv) comprises dipping the substrate in the solution of chitosan of ii), and step v) comprises dipping the one layer coated substrate obtained in step iv) in the solution of oxidized cellulose of iii).

The substrate is for example dipped in the chitosan solution for a determined time and then retrieved from the solution. The time during which the substrate is dipped into the solution should be sufficient for allowing the amount of solution necessary for further forming a coating to contact and attach to the negatively charged surface of the substrate. For example, this time may range from 5 to 60 minutes. In embodiments, this time is about 15 minutes. The substrate coated with this first layer is then washed, for example in water. This first layer may show a thickness ranging from 0.5 to 10 nm.

The substrate is then for example dipped in the oxidized cellulose solution for a determined time and then retrieved from the solution. Like for the first layer, the time during which the one layer coated substrate is dipped into the solution should be sufficient for allowing the amount of solution necessary for further forming a coating to contact and attach to the positively charged surface of the first layer of the now coated substrate. For example, this time may range from 1 to 60 minutes. In embodiments, this time is about 15 minutes. The substrate coated with the first and second layers is then washed, for example in water. The second layer may show a thickness ranging from 0.5 to 10 nm.

These operations may be repeated as many times as necessary, alternating the dipping of the two/three/four/ . . . -layer coated substrate in the chitosan solution and in the oxidized cellulose solution.

In other embodiments, each layer may be applied on the substrate and/or the previous layer by a brush previously dipped in the solution of the component, chitosan or oxidized cellulose, intended to be applied. For example, step iv) comprises applying on said substrate said solution of chitosan of ii) by means of a brush previously dipped in said solution of chitosan, and step v) comprises applying on said one layer coated substrate obtained in step iv) the solution of oxidized cellulose of iii) by means of a brush previously dipped in said solution of oxidized cellulose.

Alternatively, in other embodiments, each solution of a component, chitosan or oxidized cellulose, may be sprayed onto the substrate and/or previous layer. For example, step iv) comprises spraying on said substrate said solution of chitosan of ii), and step v) comprises spraying on said one layer coated substrate obtained in step iv) the solution of oxidized cellulose of iii).

The implants of the invention may be used as bioresorbable or partly-bioresorbable wall reinforcements, for example, in the repair, reinforcement or replacement of soft tissues when a permanent implant is not necessary, e.g. treatment of hernias, reconstruction of a wall, such as a visceral wall. They may also be used as haemostatic patches in order to stop blood bleeding.

The implants of the invention may also be used in vitro as a tissue engineering product or support for culturing live cells.

The implants of the invention may also be used as a barrier against the post-surgical adhesions.

The examples that follow illustrate the invention.

EXAMPLES

Example 1

Preparation of a Chitosan Solution: Solution A 0.111 g of chitosan (degree of acetylation 30%, molecular weight of 500 000 g/mol) is dissolved in 100 g of water with a stoichiometric amount of acetic acid ($CH_3COOH$) in order to obtain a solution of chitosan at 0.1% and pH 5.

Preparation of an Oxidized Cellulose Solution: Solution B 288.7 mg of oxidized cellulose (degree of oxidation 0.6) prepared according to WO2006/018552, is dissolved in 100 g of water together with 1.213 g of soda (NaOH). The pH of the solution is 11.8. Chlorohydric acid (HCl) at 0.2 M is added in order to obtain a solution of oxidized cellulose at 1 g/l and pH 5.

Sodium chloride (NaCl) is added to each of the solution above in order to obtain a final concentration of the component (chitosan or oxidized cellulose) in the solution of 0.25 M.

A sample textile of oxidized cellulose (degree of oxidation 0.6), prepared according to WO2006/018552, of 3 cm×3 cm such as the textile 1 shown on FIG. 1A is provided as a substrate for preparing an implant. The textile 1 is preferably an openwork textile. The surface of the textile 1 is negatively charged. The substrate consists in said textile and is therefore bioresorbable.

The textile 1 is dipped during 15 minutes in Solution A as shown on FIG. 1B. The textile 1 is then removed from Solution A and washed during 1 min in water. This washing step is repeated twice.

A textile 1 coated with a first layer 2 of chitosan is obtained, as shown on FIG. 1C.

The surface 2a of the first layer 2 is positively charged.

The textile 1 coated with the layer 2 of chitosan is then dipped in Solution B during 15 minutes, as shown on FIG. 1D. The textile 1 is then removed from Solution B and washed during 1 min in water. This washing step is repeated twice.

A textile 1 coated with a first layer 2 of chitosan and a second layer 3 of oxidized cellulose is obtained, as shown on FIG. 1E. This coated textile forms an implant 10 according to the invention.

A first sample of an implant 10, herein after referred to as Implant A, is kept for tests described below in Example 2.

Another sample of an implant 10 is then dipped again in Solution A during 15 minutes, as shown on FIG. 2A. The sample textile is then removed from Solution A and washed during 1 min in water. This washing step is repeated twice.

A textile 1 coated with a first layer 2 of chitosan, a second layer 3 of oxidized cellulose and a third layer 4 of chitosan is obtained, as shown on FIG. 2B. This coated textile forms another implant according to the invention, namely an implant 11. A sample of the implant 11, herein after referred to as Implant B, is kept for tests described below in Example 2.

Implant A and Implant B may be used as haemostatic patches or as adhesion prevention barriers. Implant A and B are bioresorbable.

In other embodiments not described, each layer may be applied on the textile and/or the previous layer by a brush previously dipped in the solution of the component, chitosan or oxidized cellulose, intended to be applied. Alternatively, each solution of a component, chitosan or oxidized cellulose, may be sprayed onto the textile and/or previous layer.

Example 2

In addition to Implant A and Implant B of Example 1, a non coated sample textile 1 of oxidized cellulose, such as the one of Example 1, is provided (herein after referred to as Textile A).

Implants A and B (invention) and Textile A (comparative) are immersed in a phosphate buffered saline (close to physiological fluid) solution.

After three days of immersion, Textile A has completely disappeared. On the contrary Implants A and B are still present in the phosphate buffered saline solution.

After seven days of immersion, Implants A and B are still present in the phosphate buffered saline solution.

The multilayer coated implants (Implants A and B) of the invention allow providing a bioresorbable or partly bioresorbable implant comprising oxidized cellulose, and thus showing the properties of oxidized cellulose, with a prolonged lifetime in a phosphate buffered saline solution, and thus in physiological fluids such as those present in a human body when the implant is implanted.

The invention claimed is:

1. An implant comprising:
   a substrate comprising a surface comprising at least oxidized cellulose, said oxidized cellulose having a degree of oxidation ranging from 0.5 to 1, and
   a multilayer coating covering said substrate, said multilayer coating comprising at least a first layer adjacent said surface of said substrate, said first layer being formed of chitosan, and a second layer adjacent said first layer, said second layer being formed of oxidized cellulose having a degree of oxidation ranging from 0.5 to 1, wherein the degree of oxidation of oxidized cellulose is the ratio of oxidized $C_6$ primary alcohol groups to oxidizable $C_6$ primary alcohol groups.

2. The implant according to claim 1, wherein said substrate is a porous layer.

3. The implant according to claim 1, wherein said substrate is an openwork textile.

4. The implant according to claim 1, wherein said chitosan has a degree of acetylation of 30%.

5. The implant according to claim 1, wherein said oxidized cellulose has a degree of oxidation of 0.6.

6. The implant according to claim 1, wherein said oxidized cellulose is amorphic.

7. The implant according to claim 1, wherein said multilayer coating further comprises a third layer adjacent said second layer, said third layer being formed of chitosan.

8. The implant according to claim 7, wherein said multilayer coating further comprises a fourth layer adjacent said third layer, said fourth layer being formed of oxidized cellulose having a degree of oxidation ranging from 0.5 to 1.

9. The implant according to claim 8, wherein said multilayer coating further comprises a fifth layer adjacent said fourth layer, said fifth layer being formed of chitosan.

10. The implant according to claim 1, wherein said implant is bioresorbable.

11. The implant according to claim 10, wherein said substrate consists of said oxidized cellulose having a degree of oxidation ranging from 0.5 to 1.

12. The implant according to claim 10, wherein said substrate consists of an openwork textile of oxidized cellulose having a degree of oxidation ranging from 0.5 to 1.

13. The implant according to claim 1, wherein a surface of the substrate is negatively charged.

14. The implant according to claim 13, wherein the substrate further comprises polysaccharides.

15. The implant according to claim 14, wherein the polysaccharides are selected from the group consisting of alginate, hyaluronan and combinations thereof.

16. The implant according to claim 1, wherein the substrate further comprises a neutral material.

17. The implant according to claim 16, wherein the neutral material comprises a non-bioresorbable material selected from the group consisting of polypropylene, polyethylene terephthalate and combinations thereof.

18. The implant according to claim 16, wherein the neutral material comprises a bioresorbable material selected from the group consisting of polylactic acid, polyglycolic acid and combinations thereof.

* * * * *